(12) United States Patent
Podszun et al.

(10) Patent No.: US 6,521,707 B2
(45) Date of Patent: Feb. 18, 2003

(54) ISOCYANATES CONTAINING AMINO GROUPS

(75) Inventors: Wolfgang Podszun, Köln (DE); Joachim Krüger, Monheim (DE); Kamelia Karlou-Eyrisch, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/004,038

(22) Filed: Nov. 1, 2001

(65) Prior Publication Data

US 2002/0156228 A1 Oct. 24, 2002

(30) Foreign Application Priority Data

Nov. 6, 2000 (DE) .......................................... 100 54 934

(51) Int. Cl.⁷ .................................................. C08F 8/30
(52) U.S. Cl. ...................... 525/123; 548/568; 546/247; 540/610; 436/161; 210/656; 435/6; 525/61; 560/129; 560/350
(58) Field of Search ................................ 560/129, 350; 525/123, 61; 435/6; 210/656; 436/161; 540/610; 546/247; 548/568

(56) References Cited

U.S. PATENT DOCUMENTS

| | | | | |
|---|---|---|---|---|
| 3,573,913 A | * | 4/1971 | Willems et al. | |
| 3,912,770 A | * | 10/1975 | Botta et al. | |
| 4,745,212 A | * | 5/1988 | Mormann et al. | |
| 4,904,750 A | * | 2/1990 | Reiners et al. | |
| 5,310,849 A | * | 5/1994 | Buysch et al. | |

FOREIGN PATENT DOCUMENTS

| | | |
|---|---|---|
| DE | 2120090 | 6/1972 |
| GB | 1354852 | 5/1974 |

OTHER PUBLICATIONS

Mormann, W., Hoffmann, S., Hoffmann, W., "Synthese und Stabilisierung von Isocyanatoketenen", Chem. Ber., 120:285–290 (1987).

\* cited by examiner

*Primary Examiner*—Rachel Gorr
(74) *Attorney, Agent, or Firm*—Jerrie L. Chiu; Susan M. Pellegrino

(57) ABSTRACT

The invention relates to novel isocyanates containing tertiary amino groups, a process for preparing them, and also their use for the synthesis and modification of polymers. The invention provides isocyanates of the formula (I)

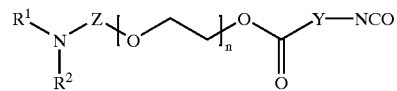

where $R^1$ and $R^2$ are, independently of one another, alkyl having from 1 to 6 carbon atoms, where $R^1$ and $R^2$ may be joined to form a ring, Z is alkylene having from 2 to 6 carbon atoms, n is an integer from 0 to 20, Y is alkylene having from 2 to 6 carbon atoms.

The alkyl radicals $R^1$ and $R^2$ may be linear or branched or joined to form an aliphatic ring. The alkylene radical Z preferably contains from 2 to 4 carbon atoms.

6 Claims, No Drawings

ISOCYANATES CONTAINING AMINO GROUPS

The invention relates to novel isocyanates containing tertiary amino groups, a process for preparing them, and also their use for the synthesis and modification of polymers.

The invention provides isocyanates of the formula (I)

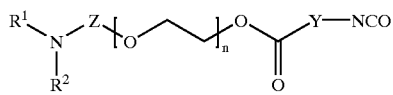

where
- $R^1$ and $R^2$ are, independently of one another, alkyl having from 1 to 6 carbon atoms, where $R^1$ and $R^2$ may be joined to form a ring,
- Z is alkylene having from 2 to 6 carbon atoms,
- n is an integer from 0 to 20,
- Y is alkylene having from 2 to 6 carbon atoms.

The alkyl radicals $R^1$ and $R^2$ may be linear or branched or joined to form an aliphatic ring, preferably a 5-membered or 6-membered ring. Preference is given to alkyl radicals having from 1 to 4 carbon atoms, and particular preference is given to methyl.

The alkylene radical Z preferably contains from 2 to 4 carbon atoms, particularly preferably 2 carbon atoms. n is preferably from 0 to 10, particularly preferably from 1 to 6.

Preference is given to isocyanates of the formula (II)

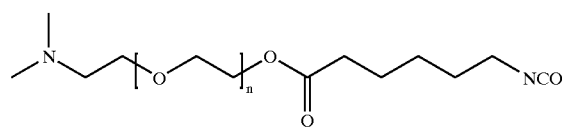

where n=0 to 20, preferably from 0 to 10, particularly preferably from 1 to 6.

Examples of isocyanates according to the invention are the following compounds:

TABLE 1

Compound 1

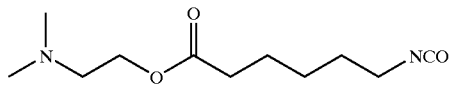

Compound 2

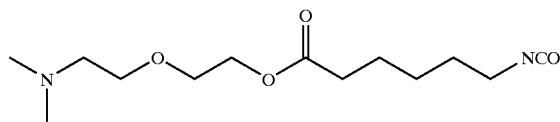

Compound 3

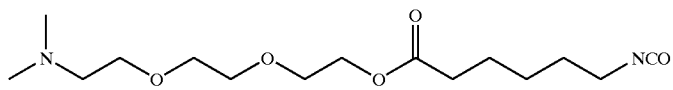

Compound 4

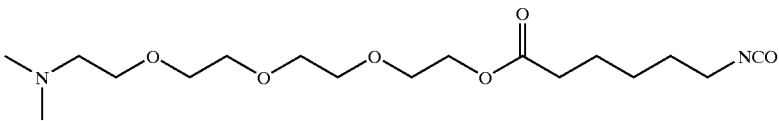

Compound 5

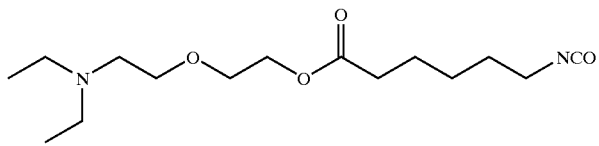

Compound 6

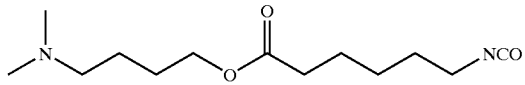

Compound 7

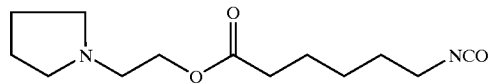

TABLE 1-continued

Compound 8

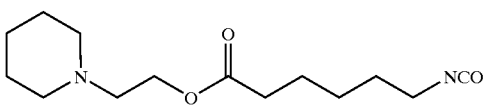

Compound 9

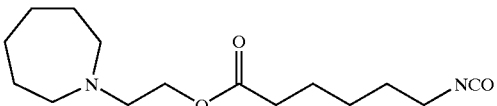

The present invention further provides a process for preparing isocyanates of the formula (1), which is characterized in that silyl compounds of the formula (III)

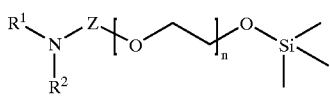

are reacted with isocyanatocarboxylic chlorides of the formula (IV),

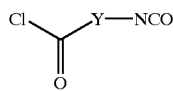

where $R^1$, $R^2$, Z, n, and Y are as defined above.

Silyl compounds of the formula (III) can be obtained by silylation of the corresponding hydroxyl compounds. Suitable hydroxyl compounds are, for example, 2-dimethylaminoethanol, 2-diethylaminoethanol, 2-dioctylaminoethanol, 3-dimethyl-aminopropanol, 3-diethylaminopropanol, 3-dibutylaminopropanol, 4-dimethylamino-butanol, 4-diethylaminobutanol, 5-dimethylaminopentanol, 6-dimethylaminohexanol, N-(2-hydroxyethyl)pyrrolidine, N-(2-hydroxyethyl)piperidine, N-(3-hydroxypropyl)-piperidine, N-(2-hydroxyethyl)hexamethylenmine, and also their ethoxylation products. Trimethylchlorosilane is a useful silylating agent for the purposes of the invention. Also useful are mixtures of trimethylchlorosilane and hexamethyl-disilazane. The parent hydroxy compounds in which n=1 to 20 can be obtained in a manner known per se by ethoxylation. It has been found that the use of strong acid ion exchangers is very useful for the isolation and purification of the ethoxylation products.

Isocyanatocarboxylic chlorides of the formula (IV) are known and can be prepared, for example, by reaction of aminocarboxylic acids with phosgene. Further details of the synthesis are described in W. Mormann, S. Hoffmann, W. Hoffmann, Chemische Berichte 120, 285–290 (1987) and in DE-A 2 120 090.

The reaction of the silyl compound of the formula (III) with the isocyanatocarboxylic chloride of the formula (IV) can be carried out in bulk without solvent. The reaction is exothermic and is preferably commenced at a low temperature of, for example, from 0° to 30° C. To control the exothermic reaction, it is advantageous for one of the reaction components, preferably the isocyanatocarboxylic chloride, to be added over a period of from 10 to 100 minutes. After the addition is complete, the reaction temperature is increased, for example to from 80 to 150° C. To remove the trimethyl-chlorosilane formed, a slight vacuum of from 50 to 500 mbar can be employed. The conversion can be monitored by quantitative determination of the trimethylsilyl chloride liberated.

The isocyanates of the invention can be reacted with hydroxy and amino compounds ($NH_2$ or NH) to form urethanes or ureas. The use of a catalyst is generally not necessary. However, known catalysts such as dibutyltin laurate, triphenylstibine or triphenylphosphine can be used if desired. The catalysts are then used in amounts of from 50 to 5000 ppm, based on the starting materials.

The isocyanates of the invention are particularly useful for carrying out polymer-analogous reactions. Thus, tert-amino groups can be introduced in a simple manner into existing polymers containing OH or $NH_2$ groups. Particulate, crosslinked or uncrosslinked polymers, for example bead polymers, can also be reacted or modified with the isocyanates of the invention. The modification of magnetic, in particular superparamagnetic, bead polymers is also possible. In the reaction with crosslinked bead polymer, a swelling agent such as chloroform, methylene chloride or methyl ethyl ketone is employed to achieve high conversions.

Bead polymers which have been modified by means of the isocyanates of the invention can be used for numerous applications. Examples which may be mentioned are use as ion exchangers, as static phase in chromatography or for the isolation of nucleic acids in diagnostics.

EXAMPLE 1

Reaction of Dimethylaminoethanol with Ethylene Oxide 887 g of dimethylaminoethanol (DMAE) were weighed into a 5 1 VA pressure 5 reactor under nitrogen and heated to 120° C. A total of 1535 g of ethylene oxide (EO) were injected a little at a time over a period of 6 hours. After cooling and venting, 2031 g of a coloured viscous mixture of dimethylarninoethanol extended with ethylene oxide were obtained.

The mixture was then purified by distillation in a high vacuum using a 1.5 m long silver-jacketed column with column head at a bath temperature of from 70 to 240° C. 3 fractions having constant boiling points were obtained.

Fraction 1: 387 g, boiling point at 0.15 mbar, 45° C., DMAEx1 EO (identification by elemental analysis and NMR spectrum)

Fraction 2: 319 g, boiling point at 0.15 mbar, 70° C., DMAEx2 EO (identification by elemental analysis and NMR spectrum)

Fraction 3: 128 g, boiling point at 0.15 mbar, 110° C., DMAEx3 EO (identification by elemental analysis and NMR spectrum)

To purify the fractions 1, 2 and 3, further, 15 g of product were in each case introduced into a column filled with 200 ml of water and 500 ml of the cation exchanger Lewatit SP 112 WS (H form). After application of the products, the column was rinsed with 2 l of deionized water. The column was subsequently eluted with 1.5 l of 6.5% strength ammonia solution. The eluate obtained was collected and subsequently evaporated at 55° C. at 15 mbar on a rotary evaporator. About 12 g of purified fractions 1 to 3 were obtained.

EXAMPLE 2

Preparation of Silyl Compounds 0.4 mol of hydroxy compound were dissolved in 400 ml of dried tert-butyl methyl ether. 32.6 g of trimethylchlorosilane and 48.42 g of hexamethyldisilazane were added dropwise to this solution over a period of 30 minutes. The mixture was stirred until (17 h) no OH band was visible in the IR spectrum. The white precipitate was filtered off and the solution was extracted 3 times with 400 ml each time of water. The organic phase was separated off, dried over magnesium sulphate and freed of solvent at 40° C. in a water pump vacuum, giving the silyl compound as a colourless oil in the amount indicated below.

|  | A | B | C | D | E |
|---|---|---|---|---|---|
| Hydroxy compound | N,N-dimethyl-aminoethanol | purified fract. 1 from Example 1 | purified fract. 2 from Example 1 | purified fract. 3 from Example 1 | N-(2-hydroxyethyl) pyrrolidine |
| Yield of silyl compound | 63.2 g | 80.4 g | 97.0 g | 115.6 g | 72.6 g |

EXAMPLE 3

Preparation of Isocyanates According to the Invention (Compounds 1 to 4 from Table 1)

In each case, 0.2 mol of the silyl compound from Example 2 was placed in a stirred vessel with exclusion of moisture. 35.12 g of isocyanatocaproyl chloride were added dropwise at 25° C. over a period of 30 minutes. During this addition, the temperature rose to 45–55° C. A reduced pressure of 250 mbar was applied and the mixture was stirred at 90° C. for 7 hours and then at 110° C. for 16 hours. The trimethylchlorosilane formed was collected in a cold trap and weighed. The compounds 1 to 4 from Table 1 remained in the reaction vessel as highly viscous oils in the amounts indicated below. The compounds were characterized by elemental analysis and NMR spectroscopy.

|  | A | B | C | D |
|---|---|---|---|---|
| Starting compound | Silyl compound from Example 2A | Silyl compound from Example 2B | Silyl compound from Example 2C | Silyl compound from Example 2D |
| Isocyanate according to the invention | compound 1 from Table 1 | Compound 2 from Table 1 | compound 3 from Table 1 | compound 4 from Table 1 |
| Yield | 43.2 g | 51.6 g | 60.0 g | 68.5 g |

EXAMPLE 4

Preparation of an Isocyanate According to the Invention 0.2 mol of the silyl compound from Example 2D was reacted with 35.12 g of isocyanatocaproyl chloride as described in Example 3. This gave 48.0 g of a highly viscous oil which was identified as compound 7 of Table 1 by elemental analysis and NMR spectroscopy.

EXAMPLE 5

Preparation of a Bead Polymer Containing OH Groups 120 ml of deionized water were placed in a 250 ml glass reactor and 1.5 g of disodium hydrogen phosphate decahydrate and 5 g of polyvinyl alcohol (degree of saponification: 88%) were dissolved therein at room temperature. While stirring at 450 rpm, a mixture of 10.5 g of methyl methacrylate, 4 g of hydroxyethyl methacrylate, 0.5 g of ethylene glycol dimethacrylate, 0.3 g of azobisisobutyronitrile and 37.5 g of chloroform was added. A nitrogen stream of 6 l/h was passed into the reaction vessel. The mixture was held at 70° C. for 21 hours and then cooled to room temperature. The reaction mixture was then transferred to glass beakers and diluted with 1 l of water. The bead polymer formed settled out completely within 4 hours. The supernatant liquid was decanted off and discarded. The bead polymer was washed 4 times with 1 l each time of water and then twice with [lacuna] each time of acetone and dried to constant weight at room temperature under reduced pressure. This gave 13.5 g of bead polymer having a mean particle size of 28 µm and an OH number of 115 mg KOH/g.

EXAMPLE 6

Modification of a Bead Polymer 10 g of bead polymer from Example 4 and 10 mg of dibutyltin dilaurate were slurried in 100 ml of dried chloroform and allowed to stand and swell for 10 hours. 4.18 g of isocyanate from Example 3B were added all at once to this suspension and the mixture was stirred at 40° C. until isocyanate could no longer be detected by IR spectroscopy (22 h). After cooling, the bead polymer was isolated by filtration, washed twice with 200 ml each time of chloroform and twice with 200 ml each time of acetone and dried to constant weight at room temperature under reduced pressure. 13.1 g of bead polymer,were obtained. Titration with 0.1 N hydrochloric acid indicated 1.1 mmol of strongly basic groups/g.

What is claimed is:

1. Isocyanates of the formula (I)

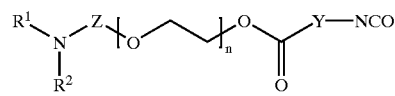

where

R$^1$ and R2 are, independently of one another, alkyl having from 1 to 6 carbon atoms, where R$^1$ and R$^2$ may be joined to form a ring, Z is alkylene having from 2 to 6 carbon atoms, n is an integer from 0 to 20, Y is alkylene having from 2 to 6 carbon atoms.

2. Isocyanates of the formula (II)

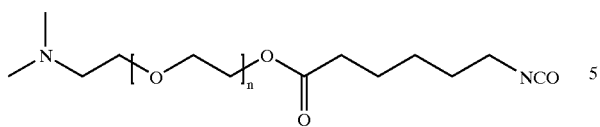

where n is an integer from 0 to 20.

3. Process for preparing isocyanates according to claim 1, characterized in that silyl compounds of the formula (III)

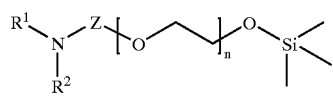

are reacted with isocyanatocarboxylic chlorides of the formula (IV),

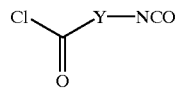

where $R^1$, $R^2$, Z, n and Y are as defined above in claim 1.

4. Reaction products of isocyanates according to claim 1 or 2 with OH—, NH—or $NH_2$-functional polymers.

5. Reaction products of isocyanates according to claim 1 or 2 with OH—, NH—or $NH_2$-functional bead polymers.

6. A method of isolating nucleic acids, comprising contacting said nucleic acids with the reaction products of claim 5.

* * * * *